US00PP34538P3

(12) United States Plant Patent
Bourne

(10) Patent No.: US PP34,538 P3
(45) Date of Patent: Sep. 6, 2022

(54) GRAPEVINE NAMED 'SV28-100-202'

(50) Latin Name: *Vitis vinifera*
Varietal Denomination: 'SV28-100-202'

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 16/350,685

(22) Filed: Dec. 18, 2018

(65) Prior Publication Data

US 2020/0196502 P1 Jun. 18, 2020

Related U.S. Application Data

(60) Provisional application No. 62/708,981, filed on Dec. 28, 2017.

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/0812; A01H 5/00; A01H 5/02; A01H 5/08; A01H 5/0806; A01H 6/88
See application file for complete search history.

*Primary Examiner* — June Hwu
(74) *Attorney, Agent, or Firm* — Eric C. Cole; Baker Manock & Jensen, PC

(57) ABSTRACT

A new and distinct variety of grapevine plant named 'SV28-100-202' particularly characterized by its ellipsoidal shaped, seedless red berries which are very large, sweet and have crisp texture. Productivity is very high with shoots producing one or two clusters on spur pruned vines.

2 Drawing Sheets

Latin name of the genus and species of the plant claimed: The plant claimed relates to a new and distinct variety of *Vitis vinifera*.

Variety denomination: The plant claimed shall be known as 'SV28-100-202'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV28-100-202'. As used herein, 'grapevine' refers to all plant parts including, vines, canes, tendrils, leaves, fruit and roots of grapevine named 'SV28-100-202'. Grapevine named 'SV28-100-202' is the result of an effort to produce a red, seedless table grape with fruit characteristics superior to currently available red skinned cultivars. This new cultivar originated from a cross conducted in May 2007 near McFarland, Calif. between pistillate grapevine plant selection 'SV18-9-1' (unpatented) and pollen parent 'Princess' (unpatented). Resultant ovules from the cross were harvested 42 days after pollination and cultured on 'McCown's Woody Plant Medium' at a temperature of 22° C. for twelve weeks. Subsequently, the resultant embryonic plants were cultured in the same medium in the laboratory under twelve hours of light from standard fluorescent lamps at 26.4° C. The seedlings from this effort were transplanted to the greenhouse in October of 2010 and grown in the greenhouse at 26.4° C. with 12 hours' illumination under high pressure sodium vapor lamps. The seedling population of 960 plants was planted in the field in the spring of 2008 near Delano, Calif. The new grapevine was selected from this seedling population on Sep. 21, 2010. It was then propagated by cuttings and bench grafted to 'Freedom' (unpatented) rootstock in 2012. The present invention has been found to retain its distinctive characteristics through two successive asexual propagations.

Grapevine named 'SV28-100-202' differs from the female parent grapevine named 'SV18-9-1' (unpatented) in that grapevine named 'SV28-100-202' has perfect flowers with functional pollen whereas it parent 'SV18-9-1' is functionally pistillate.

Grapevine named 'SV28-100-202' differs from its male parent 'Princess' (unpatented) in that grapevine named 'SV28-100-202' has dark red skinned berries while 'Princess' (unpatented) had green skinned berries.

Grapevine named 'SV28-100-202' differs from the commercial cultivar 'Scarlet Royal' (U.S. Plant Pat. No. 16,229) in that grapevine named 'SV28-100-202' has smaller berries and a very loose cluster while 'Scarlet Royal' (U.S. Plant Pat. No. 16,229) clusters are well-filled though not compact. Grapevine named 'SV28-100-202' produces berries with no astringent flavour whereas 'Scarlet Royal' (U.S. Plant Pat. No. 16,229) produces berries at full ripeness which have an astringent flavor. Additionally, Grapevine 'SV28-100-202' produces berries with very small, soft seed traces about 1 mm in length while 'Scarlet Royal' (U.S. Plant Pat. No.

16,229) produces berries with larger, more noticeable seed traces which are about 5 mm in length and partially lignified.

SUMMARY OF THE INVENTION

The following are the most outstanding and distinguishing characteristics of the ripe fruit of this new variety when grown under normal horticultural practices near McFarland, Calif. Some of the characteristics may vary depending upon changes in crop load and change of location of cultivation.

1. Bright red berry color;
2. Very firm berry texture; and
3. Very large, ellipsoidal shaped berries with sweet taste.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The first photo was taken in 2016 of a cluster of fruit and a shoot from a plant about 6 years-old, grown in a field near McFarland, Calif. The second photograph of a four year old plant was taken in a field near McFarland, Calif. in 2014.

DETAILED BOTANICAL DESCRIPTION

Figure 1:
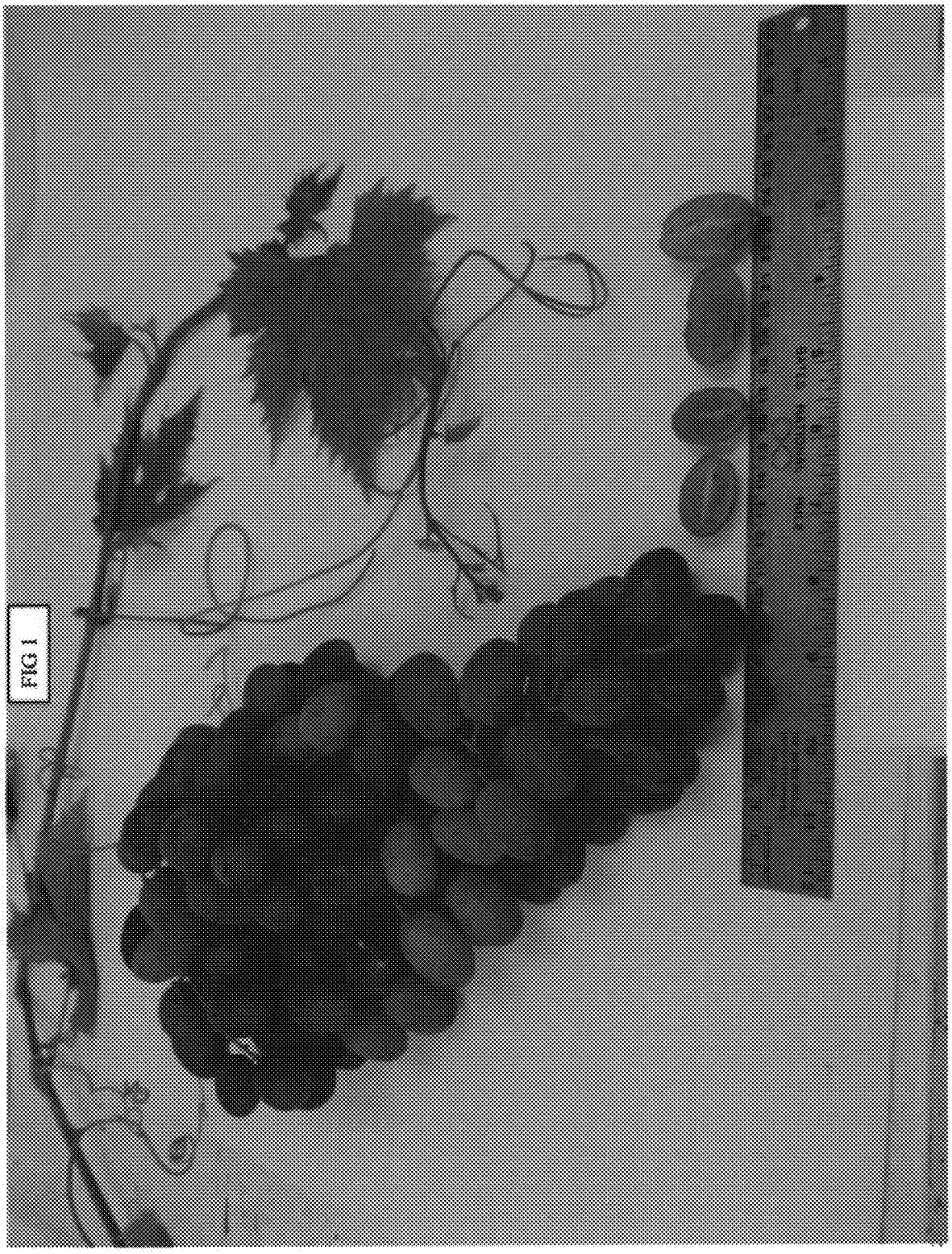
FIG. 1 Natural fruit cluster with shoots, leaves, tendrils and shoot tips.
Figure 2:
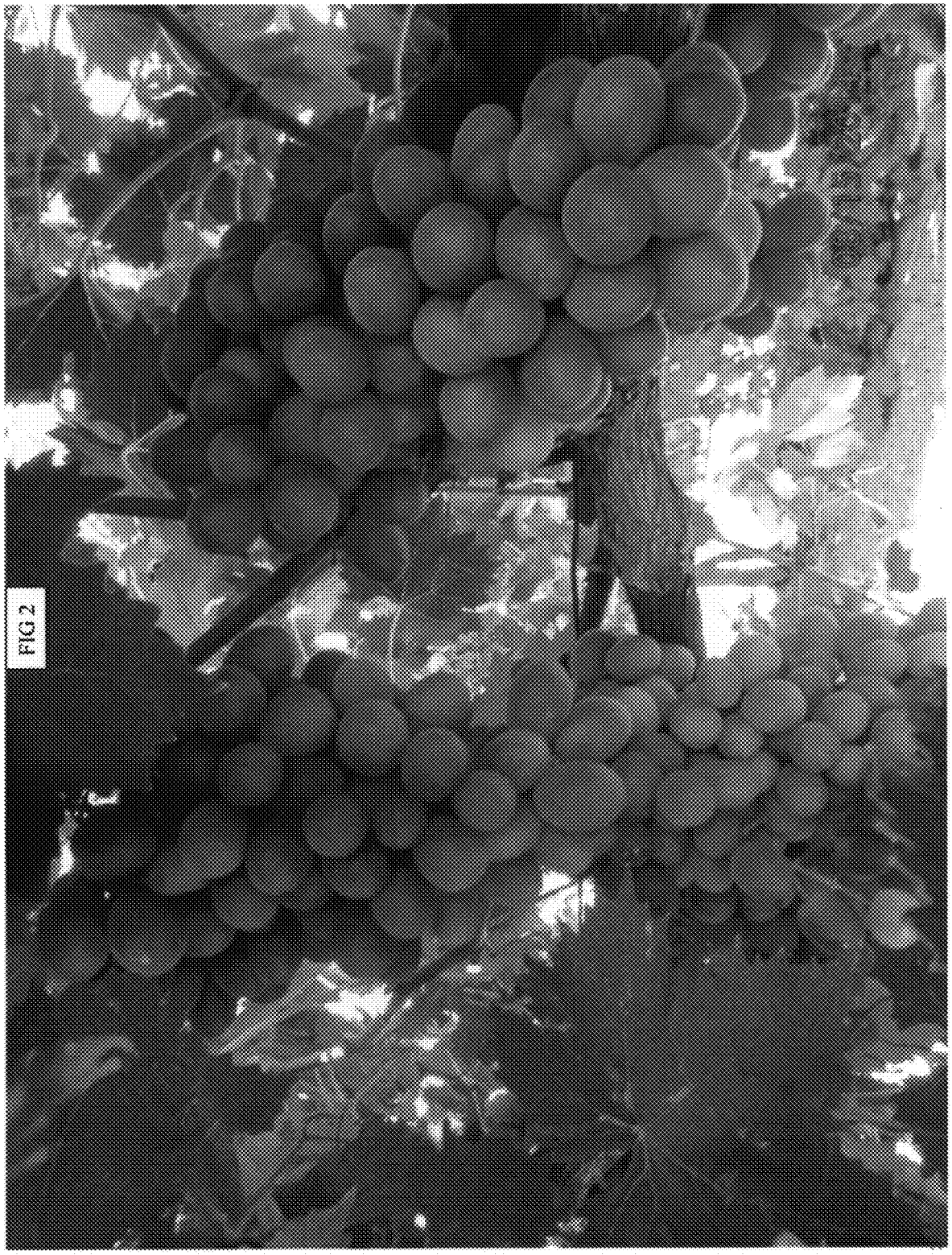
FIG. 2 Fruit clusters on vine sprayed with gibberellic acid and trunk girdled.

The following detailed description sets forth the distinctive characteristics of 'SV28-100-202'. Descriptions of the new invention apply to vines of 'SV28-100-202' grown on 'Freedom' rootstock at a density of 1,537 vines per hectare grown near McFarland, Calif. in 2017. These vines were in their sixth year of full production, having been planted in 2011. These descriptions are believed to apply generally to the new variety grown under similar circumstances elsewhere. References to color correspond to The Royal Horticultural Society's Colour Chart, The Royal Horticultural Society, London, United Kingdom (1966, 1986, 1995, 2001.). Descriptors used herein conform to those set forth by the International Board for Plant Genetic Resources Institute Grape Descriptors (*Vitis* spp.) of 1983 and/or 1997 which were developed in collaboration with the Office Interantional de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.
*Botanical name*.—*Vitis vinifera*.
*Variety name*.—'SV28-100-202'.

Plant:

*Vigor*.—Medium; vines spur-pruned and shoot thinned to 32 shoots.
*Density of foliage*.—Moderate.
*Productivity*.—Very productive when spur pruned, up to 32,000 kg/hectare.
*Hardiness*.—Hardiness observed to 0° C.
*Rootstock*.—'Freedom' (unpatented).

Trunk:

*Shape*.—Broadly elliptical.
*Straps*.—Long, split.
*Surface texture*.—Shaggy.
*Trunk circumference*.—24.6 cm at 1.0 m of height.
*Inner bark color*.—RHS Greyed orange group 174C.
*Outer bark color*.—RHS Brown group N200B.

Mature leaves:

*Average blade length*.—15.2 cm.
*Average blade width*.—18.6 cm.
*Size of blade*.—Large.
*Shape*.—Pentagonal.
*Anthocyanin coloration of main veins on the upper side of the blade*.—Absent.
*Mature leaf profile*.—Undulating, cupped upwards and flattened within plane of blade.
*Blistering* (*upper surface*).—Absent.
*Leaf blade tip*.—In plane of blade.
*Margins*.—Lobed, serrated, undulating.
*Lobes* (*average*).—Five.
*Apex*.—Narrowly acute.
*Bases*.—Sagittate.
*Thickness*.—Medium.
*Undulation of blade between main and lateral veins*.—Slight.
*Shape of teeth*.—Broadly conical, both sides convex.
*Length of teeth*.—3-9 mm.
*Ratio length/width of teeth*.—About 1:1.
*General shape of petiole sinus*.—Half open.
*Tooth at petiole sinus*.—Absent.
*Petiole sinus limited by veins*.—Absent.
*Shape of upper lateral sinus*.—Closed.
*Prostrate hairs between veins* (*lower surface*).—Absent.
*Erect hairs between veins* (*lower surface*).—Absent.
*Prostrate hairs on main veins* (*lower surface*).—Absent.
*Density of erect hairs on main veins* (*lower surface*) .—Moderate, limited to junctions of main veins.
*Prostrate hairs on main veins* (*upper surface*).—Absent.
*Upper surface*.—Summer color: RHS Green group 137A. Surface texture: Smooth Surface appearance: Dull. Goffering of blade: Absent.
*Lower surface*.—Summer color: RHS Green group 137C. Anthocyanin coloration of main veins on lower leaf surface: Absent. Anthocyanin coloration on laterals: No. Glossiness: Low. Pubescence: Absent. Surface texture: Rough. Surface appearance: Dull.
*Petiole*.—Length: 13.5 cm. Length of petiole compared to middle vein: Slightly shorter. Density of prostrate hairs: Absent. Density of erect hairs: Absent. Shape of base of petiole sinus: Half open. Color: In shade: RHS Yellow green group 144C. In sun: RHS Yellow green group 144C with streaks of red purple group 59A.
*Buds*.—Time of leaf bud burst: Early.

Tendrils:

*Length*.—Long, averaging 24.2 cm.
*Color*.—In shade: RHS Yellow green group 144A.

Growing tips (young shoot):

*Presence of pubescence on young shoot meristematic tip*.—Sparse, prostrate.
*Color*.—RHS Yellow Green Group 144B.
*Presence of anthocyanins at shoot tip meristem*.—Absent.
*Shape*.—Flattened.

*Apex*.—Fully open.

*Shoot attitude*.—Semi-erect.

Young leaves:

*Color of young leaves, upper surface*.—RHS Yellow green group 144B.

Flowers:

*Flower sex*.—Perfect.

*Position of first flowering nodes*.—Usually on node 4.

*Number of inflorescences per shoot*.—One or two on nodes 4 and 5. Date of full bloom: May 6th.

*Flower cluster length* (*peduncle included*).—31 cm.

*Unopened flower length*.—3 mm.

*Flower pedicel length*.—3 mm.

*Calyptra color*.—Green group 143A.

*Ovary length*.—2.5 mm.

*Ovary color*.—Green group 141B.

*Anther length*.—1 mm.

*Anther color*.—Yellow group 8B.

*Filament length*.—2 mm.

*Filament color* (*absence of pigment*).—Translucent.

Fruit:

*Ripening period*.—Mid-season.

*Date of ripening*.—August 10th at McFarland, Calif.

*Use*.—Fresh market.

*Keeping quality*.—Good.

*Shipping quality*.—Good.

*Date of first harvest*.—August 10th.

*Solids-sugar*.—23 brix at full maturity.

*Refractometer test*.—20.0 brix.

*Bunch*.—Size: Medium. Length (peduncle excluded): 35.2 cm. Width: 18.7 cm. Weight: Natural, without gibberellic acid treatment: 1187 g. Density: Loose. Bunch density of natural clusters with no gibberellic acid treatment: Very loose. Number of berries: 173. Form: Cylindrical with 4 or 5 major branches from central rachis.

*Peduncle*.—Length: 7.2 cm. Lignification: Medium. Color: RHS Yellow green group 144A.

*Berry*.—Size: Large. Uniformity of size: Variable, about 3 g to 7 g. Weight: Natural, without gibberellic acid treatment: About 6.7 g. Shape: Ellipsoidal. Presence of seeds: Seedless; most berries develop one or two tiny ovule traces about 1 mm in length. Cross section: Circular. Dimensions, natural berries not treated with gibberellic acid: Longitudinal axis: About 2.7 cm. Horizontal axis: About 2.0 cm. Skin color (without bloom): RHS Red Purple Group 59A. Berry flesh color: Translucent, absence of anthocycnin. Juiciness of flesh: Very juicy. Berry firmness: Very firm. Particular flavor: Neutral, typical *Vitis vinifera* table grape. Bloom (cuticular wax): Heavy. Pedicel length: About 1.3 cm. Berry separation from pedicel: Moderately easy.

*Skin*.—Thickness: Medium. Texture: Tender. Reticulation: Absent. Roughness: Absent. Tenacity: Tenacious to flesh.

*Tendency to crack*.—Resistant.

Disease and insect resistance: Moderately susceptible to powdery mildew which may be controlled with standard fungicides in California.

Having thus described and illustrated our new variety of grapevine, I claim:

1. A new and distinct variety of grapevine plant named 'SV28-100-202', substantially as illustrated and described herein.

* * * * *